US00PP36765P2

(12) United States Plant Patent
Schoone

(10) Patent No.: US PP36,765 P2
(45) Date of Patent: Jun. 24, 2025

(54) ***PHALAENOPSIS* PLANT NAMED 'Ceremony'**

(50) Latin Name: *Phalaenopsis hybrida*
Varietal Denomination: Ceremony

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/975,946

(22) Filed: Dec. 10, 2024

Related U.S. Application Data

(60) Provisional application No. 63/608,785, filed on Dec. 11, 2023.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'Ceremony', characterized by its upright plant habit; strong flowering stems; healthy and sturdy leaves; freely flowering habit with typically two inflorescences developing per plant, each inflorescence with numerous flowers; white-colored flowers with purple-colored venation; and good postproduction longevity.

2 Drawing Sheets

Figure 1:
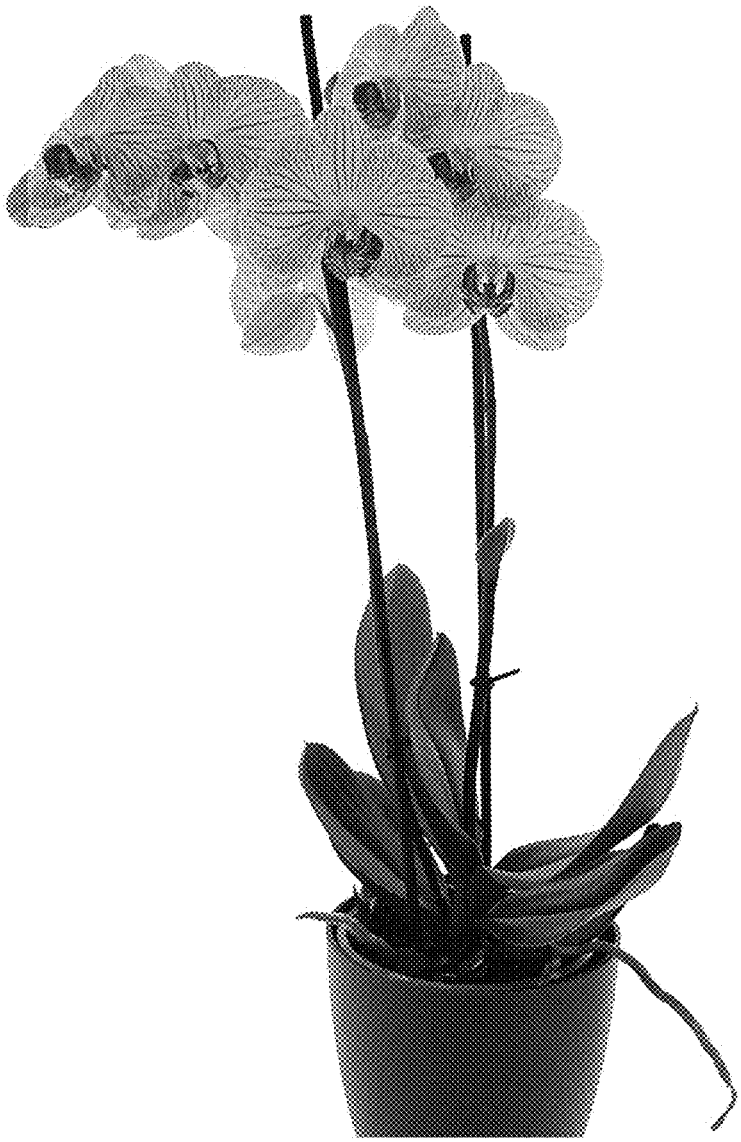

Botanical designation: *Phalaenopsis hybrida.*
Cultivar denomination: 'CEREMONY'.

CROSS-REFERENCED TO CLOSELY-RELATED APPLICATIONS

A European Community Plant Breeder's Rights application for the instant plant was filed by the Applicant/Assignee, Floricultura B.V. of Heemskerk, The Netherlands on Dec. 2, 2023, application number 2023/2620. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Ceremony'.

The new *Phalaenopsis* plant is a product of a planned breeding program conducted by the Inventor in Taichung City, Taiwan, Heemskerk, The Netherlands and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in January 2014 in Taichung City, Taiwan of *Phalaenopsis hybrida* 'Mary Stripes', not patented, as the female, or seed, parent with *Phalaenopsis hybrida* 'Arakaki Cherry Stripes', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November 2020.

Asexual reproduction of the new *Phalaenopsis* plant by in vitro meristem propagation in a controlled environment in Assendelft, The Netherlands since November 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Ceremony'. These characteristics in combination distinguish 'Ceremony' as a new and distinct *Phalaenopsis* plant:

1. Upright plant habit.
2. Strong flowering stems.
3. Healthy and sturdy leaves.
4. Freely flowering habit with typically two inflorescences developing per plant, each inflorescence with numerous flowers.
5. White-colored flowers with purple-colored venation.
6. Good postproduction longevity.

Plants of the new *Phalaenopsis* can be compared to plants of the female parent, 'Mary Stripes'. Plants of the new *Phalaenopsis* differ primarily from plants of 'Mary Stripes' in flower color as flowers of plants of the new *Phalaenopsis* are white in color with purple-colored venation whereas flowers of plants of 'Mary Stripes' are purple in color.

Plants of the new *Phalaenopsis* can be compared to plants of the male parent, 'Arakaki Cherry Stripes'. Plants of the new *Phalaenopsis* differ primarily from plants of 'Arakaki Cherry Stripes' in flower color as flowers of plants of the new *Phalaenopsis* are white in color with purple-colored venation whereas flowers of plants of 'Arakaki Cherry Stripes' are purple in color.

Plants of the new *Phalaenopsis* can be compared to plants of *Phalaenopsis hybrida* 'Razzle Dazzle', not patented. In side-by-side comparisons, plants of the new *Phalaenopsis* differ primarily from plants of 'Razzle Dazzle' in flower color as flowers of plants of the new *Phalaenopsis* have more conspicuous venation than flowers of plants of 'Razzle Dazzle'. In addition, peduncles of plants of the new *Phalaenopsis* are reddish brown in color with fine yellow green-colored dots whereas peduncles of plants of 'Razzle Dazzle' are yellow green in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Ceremony' grown in a container.

Figure 2:
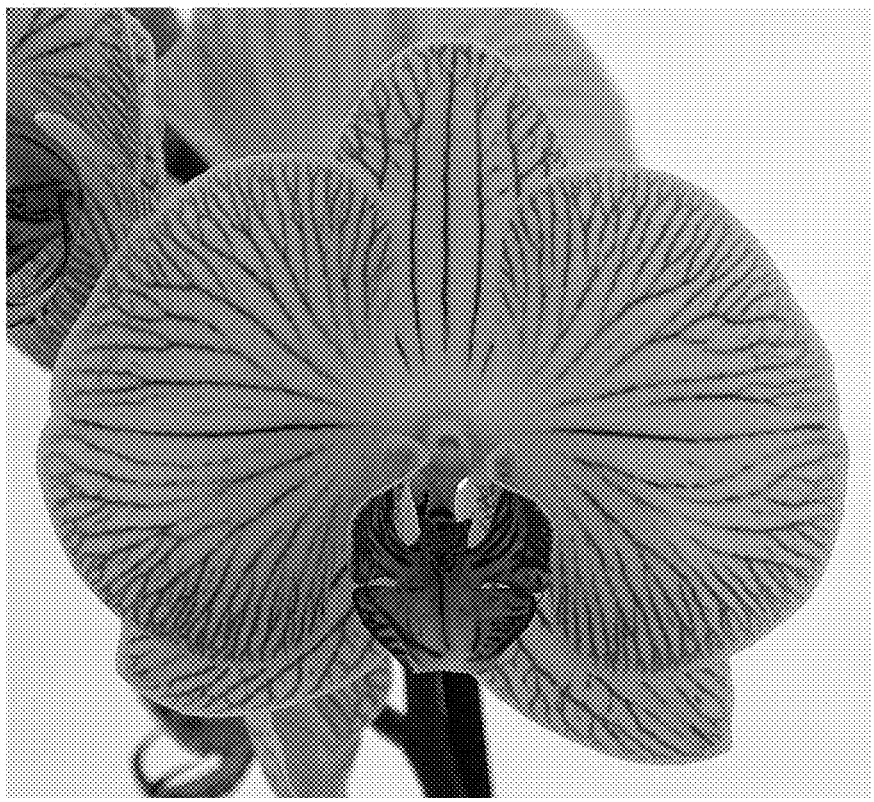

The photograph on the second sheet (FIG. 2) is a close-up view of a typical flower of 'Ceremony'.

DETAILED BOTANICAL DESCRIPTION

The aforementioned photographs and following observations and measurements describe plants grown during the early spring in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Ceremony'.

Parentage:

- *Female, or seed, parent.*—*Phalaenopsis hybrida* 'Mary Stripes', not patented.
- *Male, or pollen, parent.*—*Phalaenopsis hybrida* 'Arakaki Cherry Stripes', not patented.

Propagation:

- *Type.*—By in vitro meristem propagation.
- *Time to initiate roots, summer and winter.*—About two weeks at temperatures about 28° C. to 30° C.
- *Time to produce a rooted young plant, summer and winter.*—About 20 to 25 weeks at temperatures about 28° C. to 30° C.
- *Root description.*—Thin, fibrous; typically light yellowish white in color; actual color of the roots is dependent on substrate composition, water quality, fertilizer, substrate temperature and age of roots.
- *Rooting habit.*—Freely branching; medium density.

Plant description:

- *Plant form and growth habit.*—Herbaceous epiphyte; upright plant habit with typically two inflorescences developing per plant, each inflorescence with numerous flowers; monopodial; moderately vigorous growth habit and moderate growth rate.
- *Plant height, substrate level to top of foliar plane.*—About 16.5 cm.
- *Plant height, substrate level to top of floral plane.*—About 42.9 cm.
- *Plant diameter or spread.*—About 28.2 cm.

Leaf description:

- *Arrangement and quantity.*—Distichous, simple; sessile; about seven to eight fully-developed leaves per plant.
- *Length.*—About 15.4 cm.
- *Width.*—About 7.2 cm.
- *Aspect.*—Erect to upwardly arching.
- *Shape.*—Obovate; slightly to moderately carinate.
- *Apex.*—Unequal obtuse.
- *Base.*—Sheathing. Sheath length: About 1.9 cm. Sheath width: About 1.6 cm. Sheath color, upper and lower surfaces: Close to 143C; distal margins, tinged with close to 143B.
- *Margin.*—Entire.
- *Texture and luster, upper surface.*—Smooth, glabrous; slightly glossy.
- *Texture and luster, lower surface.*—Smooth, glabrous; matte to slightly glossy.
- *Venation pattern.*—Camptodromous.
- *Color.*—Developing leaves, upper surface: Close to NN137A. Developing leaves, lower surface: Close to 146A and 146B. Fully expanded leaves, upper surface: Close to NN137B with narrow marginal edges, close to 144B; venation, close to NN137A. Fully expanded leaves, lower surface: Close to a blend of 146B and 147B; towards the margins, close to NN137C; venation, close to 144A.

Inflorescence description:

- *Appearance and flowering habit.*—Showy zygomorphic flowers arranged on axillary simple or branched racemes; typically two inflorescences develop per plant; each inflorescence with about eight flowers; flowers face outwardly on outwardly arching inflorescences supported by upright peduncles; flowers with three petals, two lateral petals and one center petal transformed into a labellum and three sepals.
- *Fragrance.*—None detected.
- *Time to flower.*—Plants begin flowering about six months after planting; plants flower naturally during the winter into the spring.
- *Flower longevity and postproduction longevity.*—Long flowering period and good postproduction longevity, individual flowers maintain good substance for about four months on the plant; flowers not persistent.
- *Inflorescence length* (*lowermost flower to inflorescence apex*).—About 18.4 cm.
- *Inflorescence width.*—About 11.2 cm.
- *Flower buds.*—Height: About 2 cm. Diameter: About 1.5 cm by 1.8 cm. Shape: Broadly ovate. Color: Close to N144D; towards the apex, close to a blend of 146D and 152D; venation, close to 178A.
- *Flower size.*—About 7.9 cm (vertical) by 8.8 cm (horizontal).
- *Flower depth.*—About 3.2 cm.

*Petals, quantity and arrangement*.—Three, two lateral petals and one center petal transformed into a labellum.

*Lateral petals*.—Length: About 4.2 cm. Width: About 5.6 cm. Shape: Reniform to lunate-reniform. Apex: Broad obtuse and shallowly retuse. Margin: Entire. Texture and luster, upper and lower surfaces: Smooth, glabrous; moderately velvety; matte. Color: When opening, upper surface: Close to NN155B; towards the margins and apex, close to NN155D; at the base, close to 157A; conspicuous midvein, close to 71A; conspicuous lateral venation, close to NN78B and fading towards the margins and apex to closer to N78B; marginal edges without venation. When opening, lower surface: Close to 157A; towards the margins and apex, close to 157D; at the base, close to 145C; conspicuous venation, close to N78A and fading towards the margins and apex to closer to N78D; marginal edges without venation. Fully opened, upper surface: Close to NN155D; at the base, close to NN155A; conspicuous midvein, close to N78A; conspicuous lateral venation, close to NN78B and fading towards the margins and apex to closer to a blend of N78C, N78D and NN78D; marginal edges without venation; colors do not change with subsequent development. Fully opened, lower surface: Close to NN157C; at the base, close to 155C; conspicuous venation, close to N78B and fading towards the margins and apex to closer to N78C and N78D; marginal edges without venation; colors do not change with subsequent development.

*Labella*.—Appearance: Three-parted with two lateral lobes and a central lobe. Length, lateral lobes: About 2.1 cm. Width, lateral lobes: About 1.6 cm. Length, central lobe: About 2 cm. Width, central lobe: About 0.7 cm to 2 cm. Length, cirrhose apices: About 1.3 cm. Shape, lateral lobes: Obovate. Shape, central lobe: Broadly deltoid with an elongated apex. Apex, lateral lobes: Obtuse. Apex, central lobe: Acute with two cirrhose apices curled upright and backwards. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 6 mm in width and about 5 mm in height. Color: When opening, upper surface: Lateral lobes: Close to NN155D; conspicuous venation and stripes, close to N78A and fading towards the base to close to 71A; proximal margin, close to 5B; at the base, axial stripes, close to 187B; marginal edges without venation. Central lobe: Close to 151D fading towards the apex to closer to 150D with edges, close to N77A; conspicuous venation, stripes and dots, close to 61A and 71A; at the base, close to 157A with radial stripes, close to a blend of 183A and N186C; cirrhose apices, close to 61A with edges, close to NN155D. When opening, lower surface: Lateral lobes: Close to 156D; towards the margins and apex with conspicuous venation and dots, close to N78A and fading towards the base to closer to 71A; distal margin, close to NN155A; proximal margin, close to 6A and 6B; at the base, axial stripes, close to 71A. Central lobe: Close to 151D fading towards the apex to closer to a blend of 150D and 157C with edges, close to 71A; conspicuous venation, stripes and dots, close to 61A and 71A; at the base, close to 145C; cirrhose apices, close to 61A with tips, close to NN155D. Fully opened, upper surface: Lateral lobes: Close to NN155D; conspicuous venation and stripes, close to N78A and fading towards the base to closer to 71A; proximal margin, close to 5B; at the base, axial stripes, close to 187B; marginal edges without venation. Central lobe: Close to 14C fading towards the apex to closer to NN155A with edges, close to N77A; conspicuous venation, stripes and dots, close to 61B and 71A; at the base, close to 145D with radial stripes, close to 200A; cirrhose apices, close to 61A with edges, close to NN155D. Fully opened, lower surface: Lateral lobes: Close to 156D; towards the margins and apex with conspicuous venation and dots, close to N78A; distal margin, close to NN155A; proximal margin, close to 8A and 8B; at the base, axial stripes, close to 71A. Central lobe: Close to 154B fading towards the apex to closer to NN155D with narrow edges, close to 61A; conspicuous venation, stripes and dots, close to 71A and N78A; at the base, close to 144D; cirrhose apices, close to 61A with tips, close to NN155D. Callosities: When developing: Close to 4B; towards the apex, close to 9A and 9B with fine dots, close to 166A. Fully developed: Close to 9B; towards the apex, close to 13B with fine dots, close to 183A and N186C.

*Sepals*.—Quantity and arrangement: Three, one upper dorsal sepal and two lower lateral sepals. Length, dorsal sepal: About 4.3 cm. Width, dorsal sepal: About 3 cm. Length, lateral sepals: About 4.3 cm. Width, lateral sepals: About 2.7 cm. Shape, dorsal sepal: Elliptic. Shape, lateral sepals: Ovate. Apex, dorsal sepal: Obtuse. Apex, lateral sepals: Bluntly acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to 157D fading towards the base to closer to 157B; conspicuous midvein, close to 71A; conspicuous lateral venation, close to N78A fading towards the margins and apex to closer to N78B and N78C; marginal edges without venation. When opening, lower surface: Close to 151D fading towards the margins and apex to closer to 157C and 157D; conspicuous midvein, close to 182B; conspicuous lateral venation, close to N78B and N78C; marginal edges without venation. Fully opened, upper surface: Close to NN155D fading towards the base to closer to NN155B; conspicuous venation, close to N78A fading towards the margins and apex to closer to N78C; marginal edges without venation. Fully opened, lower surface: Close to 76D fading towards the margins and apex to closer to NN155C; conspicuous venation, close to 77B, 77C and 77D; marginal edges without venation. Color, lateral sepals: When opening, upper surface: Close to 157D fading towards the base to closer to 145B; conspicuous midvein, close to 71A; conspicuous lateral venation, close to N78A fading towards the margins and apex to closer to N78B; at the base, fine dots, close to 71A; marginal edges without venation. When opening, lower surface: Close to N144D fading towards the margins and apex to closer to 145C; conspicuous venation, close to 71A and fading towards the margins and apex to closer to 182B; marginal edges without venation. Fully opened, upper surface: Close to NN155D fading towards the base to closer to 145B and 145C; conspicuous midvein, close to 71A; conspicuous lateral venation, close to N78B fading towards the margins and apex to closer to N78B to N78C; at the base, fine dots, close to 71A; marginal edges without venation. Fully opened, lower surface: Close to a blend of 76D and NN155A fading towards the base to closer to 145C; conspicuous midvein, close to 77B; conspicuous lateral venation, close to 76A; marginal edges without venation.

*Peduncles*.—Length: About 40.6 cm. Diameter: About 6 mm. Strength: Strong. Aspect: Upright to slightly outwardly arching. Texture and luster: Smooth, glabrous; matte. Color: Close to 200B densely covered with fine dots, close to 148B.

*Pedicels*.—Length: About 3.2 cm. Diameter: About 3 mm. Strength: Moderately strong. Aspect: About 60° from peduncle axis. Texture and luster: Smooth, glabrous; matte. Color: Close to 146C and 146D; proximal end, close to a blend of N186C and 200B and distal end, close to 76D.

*Reproductive organs*.—Androecium: Column length: About 9 mm. Column width: About 5 mm. Column color: Close to NN155D with blotch, close to N78B. Pollinia quantity: Two. Pollinia diameter (per two pollinia): About 2.25 mm. Pollinia color: Close to 23A. Gynoecium: Stigma length: About 3 mm. Stigma width: About 4 mm. Stigma shape: Reniform. Stigma color: Close to 155C. Ovary length: About 1.2 cm. Ovary diameter: About 1 mm. Ovary color: Close to 149A and 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Ceremony' as herein illustrated and described.

* * * * *